(12) United States Patent
DeBlock et al.

(10) Patent No.: US 6,741,074 B2
(45) Date of Patent: May 25, 2004

(54) METHOD AND APPARATUS FOR SEPARATING ELECTRICAL RUNOUT FROM MECHANICAL RUNOUT

(75) Inventors: Mark John DeBlock, Peterborough (CA); W. R. Hugh Fife, Omemee (CA)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/087,871

(22) Filed: Mar. 1, 2002

(65) Prior Publication Data

US 2003/0164699 A1 Sep. 4, 2003

(51) Int. Cl.[7] .......................... G01H 11/02; G01N 27/87
(52) U.S. Cl. ........................................ 324/227; 324/226
(58) Field of Search .................................. 324/226, 227, 324/234, 236–243, 207.25, 262; 73/660, 661

(56) References Cited

U.S. PATENT DOCUMENTS

| | | | |
|---|---|---|---|
| 3,986,380 A | * | 10/1976 | Biggs ............................ 72/76 |
| 4,135,244 A | | 1/1979 | Davis |
| 4,258,319 A | | 3/1981 | Shimada et al. |
| 4,430,614 A | | 2/1984 | Gereg |
| 4,460,869 A | | 7/1984 | Buser et al. |
| 4,604,251 A | | 8/1986 | Kuhman |
| 4,644,271 A | | 2/1987 | Toth et al. |
| 4,675,605 A | | 6/1987 | Watjen |
| 4,719,422 A | | 1/1988 | DeWalle et al. |
| 5,033,305 A | * | 7/1991 | Rozelle et al. ................. 73/650 |
| 5,130,651 A | | 7/1992 | Morrey, Jr. |
| 5,140,534 A | * | 8/1992 | Miller et al. ................. 700/279 |
| 5,278,498 A | | 1/1994 | Vernon et al. |
| 5,345,514 A | | 9/1994 | Mahdavieh et al. |
| 5,389,876 A | | 2/1995 | Hedengren et al. |
| 5,473,247 A | | 12/1995 | You et al. |
| 5,648,721 A | | 7/1997 | Wincheski et al. |
| 5,696,444 A | | 12/1997 | Kipp et al. |
| 5,854,553 A | | 12/1998 | Barclay et al. |
| 5,864,229 A | | 1/1999 | Lund |
| 5,903,147 A | | 5/1999 | Granger, Jr. et al. |
| 5,926,020 A | | 7/1999 | Samson |

* cited by examiner

*Primary Examiner*—N. Le
*Assistant Examiner*—Reena Aurora
(74) *Attorney, Agent, or Firm*—Karl A. Vick, Esq.; Armstrong Teadale LLP

(57) ABSTRACT

A method for separating electrical runout from mechanical runout includes positioning at least one position probe against a rotating part, positioning at least one proximity probe adjacent the rotating part, and calculating an electrical runout based on measurements obtained from the position probe and the proximity probe.

8 Claims, 4 Drawing Sheets

METHOD AND APPARATUS FOR SEPARATING ELECTRICAL RUNOUT FROM MECHANICAL RUNOUT

BACKGROUND OF THE INVENTION

This invention relates generally to manufacturing rotating equipment and, more specifically, to inspecting rotating parts.

Rotating equipment is utilized in many manufacturing applications. Rotating equipment failures can cause lost production time, injury to personnel, and loss of capital equipment, all of which can reduce profitability. One known cause of rotating equipment failure is due to vibrations. Accordingly, some rotating equipment is operated with at least one proximity probe continually monitoring vibrations (displacement of the rotating part) to protect the equipment from damage due to excessive vibration. However, proximity probes typically introduce an error in the displacement signal thus generated. For example, an eddy current probe will introduce displacement errors due to material variations in the rotating part.

More specifically, eddy current probes derive distances utilizing induced electrical currents in the material of the rotating part and, therefore, variations in electrical properties of the material results in errors in the derived distance. This error due to variations of electrical properties is called electrical runout. Additionally, the proximity probe will read all displacements as indicative of vibrations. For example, mechanical runout (concentricity, roundness, and flatness) also is read as a displacement and is interpreted as a vibration. A common test procedure to assess the suitability of the proximity probe signal is to allow the rotating equipment to coast at a speed much less than its normal operating speed. The rational for this is that at this lower speed, vibration is essentially zero.

This test procedure is commonly referred to as the "slow roll" test. The displacement signal that the proximity probe provides during the slow roll test is considered the error in the signal. The measured error is related to the degree of mechanical runout plus electrical runout and thus does not differentiate between the two. However, known methods for correcting mechanical runout are different than known methods for correcting electrical runout and it is costly and time consuming utilizing a mechanical method for an electrical problem. Likewise, it is costly and time consuming utilizing an electrical method when the problem is mechanical runout.

BRIEF DESCRIPTION OF THE INVENTION

In one aspect, a method for separating electrical runout from mechanical runout includes positioning at least one position probe against a rotating part, positioning at least one proximity probe adjacent the rotating part, and calculating an electrical runout based on measurements obtained from the position probe and the proximity probe.

In another aspect, a method for facilitating a reduction in slow roll test failures includes measuring at least one of a concentricity value, an out of roundness value for a proximity surface of a rotor, and an out of roundness value for a journal surface of the rotor prior to the rotor being assembled in the rotating equipment. The method further includes measuring electrical runout and determining a predicted slow roll runout value of the rotor. Additionally, the method includes comparing the predicted slow roll value to a predetermined value and re-working the rotor when the predicted slow roll value exceeds the predetermined value.

In yet another aspect, inspection apparatus for a rotating part includes a data collection system and a plurality of position probes electrically coupled to the data collection system, wherein the position probes are disposed adjacent the rotating part. The apparatus further includes at least one proximity probe electrically coupled to the data collection system, wherein the proximity probe is disposed adjacent the rotating part. A computer is electrically coupled to the data collection system and is configured to calculate an electrical runout.

In a further aspect, inspection apparatus for a rotating part includes a data collection system and a plurality of position probes electrically coupled to the data collection system, wherein the position probes are disposed adjacent the rotating part. The plurality of position probes include a first probe, a second probe, a third probe and a fourth probe, the first probe is substantially 180° from the second probe, and the third probe is substantially 180° from the fourth probe. The apparatus further includes at least one proximity probe electrically coupled to the data collection system, wherein the proximity probe is disposed adjacent the rotating part. A computer is electrically coupled to the data collection system and is configured to calculate an electrical runout. The computer is further configured to determine a predicted slow roll runout for a right probe by adding a series of vectors as described later. The computer is further configured to determine a predicted slow roll runout for a left probe by adding a series of vectors as described later.

In another aspect, apparatus for predicting a slow roll test failure utilizing a data collection system includes a computer programmed to receive a plurality of probe measurements and generate at least one slow roll runout value for at least one of a left probe and a right probe.

DETAILED DESCRIPTION OF THE INVENTION

Figure 1:
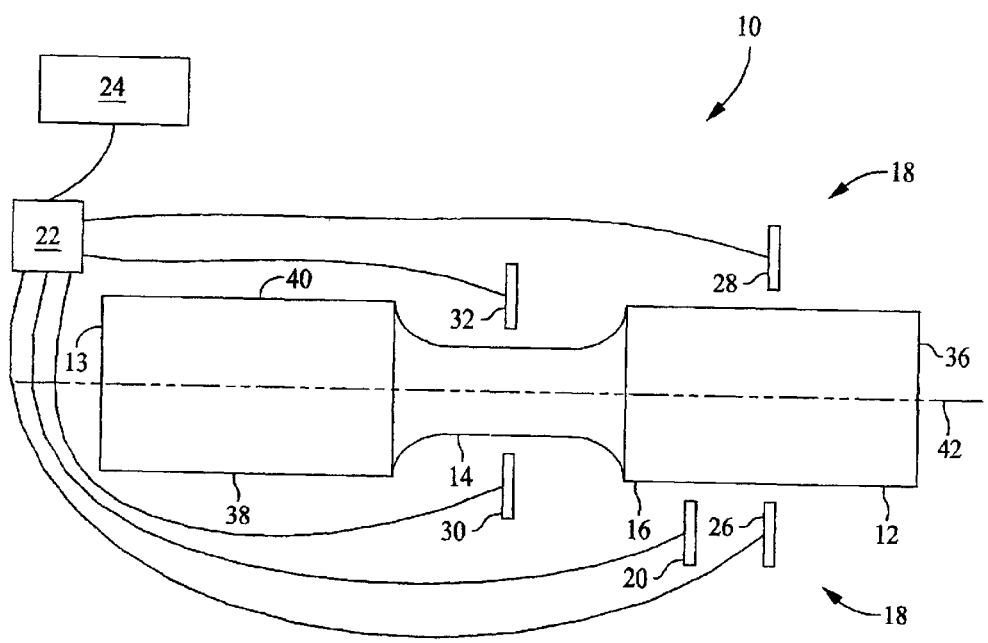
FIG. 1 is a top view of a runout separation system.
Figure 2:
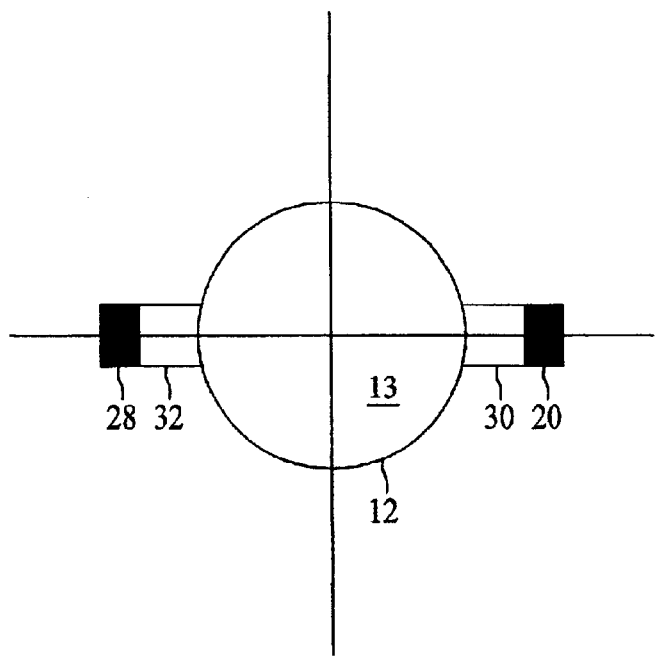
FIG. 2 is an axial view of a first end of a rotor shown in FIG. 1.

FIG. 1 is a top view of a runout separation system 10 used to facilitate a separation of mechanical runout from electrical runout for a rotating part 12 prior to part 12 being assembled in a piece of rotating equipment (not shown), and FIG. 2 is an axial view of a first end 13 of part 12. In an exemplary embodiment, part 12 is a rotor for a piece of rotating equipment. Rotor 12 includes a journal 14 and a proximity surface 16. Separation system 10 includes a plurality of position probes 18, a proximity probe 20, a data collection system 22, and a computer 24. In an exemplary embodiment, data collection system 22 is a DataPAC System 10 data collection system available from the Daytronic Corporation, and position probes 18 are linear variable differential transformers (LVDTs). Position probes 18 are any probe capable of determining a position of an object. Suitable probes include but are not limited to contact probes and LASER probes. Proximity probe 20 is any probe capable of determining a position of an object without contacting the object. In an exemplary embodiment, proximity probe is an eddy current probe. Computer 24 includes a commercially available processor (not shown) including a memory (not shown) coupled to the processor. It should be understood that the present invention can be practiced with many alternative computers, and is not limited to practice in connection with just computer 24. Therefore, and as used herein, the term computer is not limited to just those integrated circuits referred to in the art as computers, but broadly refers to computers, processors, microcontrollers, microcomputers, application specific integrated circuits, programmable logic controllers (PLCs), and other programmable circuits. Additionally, although herein described with computer 24 separate from data collection system 22, data collection system 22 and computer 24 can be combined in a single device.

Probes 18 include a first probe 26, a second probe 28, a third probe 30, and a fourth probe 32. Rotor 12 further includes a second end 36, a front side 38, a back side 40, and an axis 42. In an exemplary embodiment, first probe 26 and second probe 28 are positioned 180° apart circumferentially about proximity surface 16, and third probe 30 and fourth probe 32 are positioned 180° apart circumferentially about journal 14. In an alternative embodiment, more than four probes are utilized. In a further alternative embodiment, less than four probes are utilized. In one embodiment, probes 20 and 26 are co-linear in an axial direction. In another embodiment, all probes 20, 26, 28, 30, and 32 are co-planer.

During operation of system 10, rotor 12 rotates about axis 42 at a low number of revolutions per minute (RPM). In an exemplary embodiment, rotor 12 rotates about axis 42 at approximately 4 RPM. In an alternative embodiment, rotor 12 rotates about axis 42 at more than 4 RPM. In a further alternative embodiment, rotor 12 rotates about axis 42 at less than 4 RPM. During one complete rotation, position probes 18 take a plurality of measurements of data points (not shown), the measurements are transmitted to computer 24 via data collection system 22. In an exemplary embodiment, each position probe 18 measures at least 200 data points. Additionally, proximity probe 20 takes a plurality of measurements that are transmitted to computer 24 via data collection system 22. Computer 24 receives the measurements from data collection system 22 and creates a file for the measurements. Each data point which first probe 26 measures is also measured by second probe 28. For example, the data point that first probe 26 measures initially at a beginning of a revolution of rotor 12 is measured by second probe 28 halfway through the revolution. Accordingly, the measurements of proximity surface 16 by first probe 26 and second probe 28 can be combined to produce one waveform for the mechanical shape of the shaft. Similarly, the measurements of journal 14 by third probe 30 and fourth probe 32 can be averaged.

One measurement of mechanical runout is concentricity or how concentric proximity surface 16 is to journal 14. A front runout value is determined for each data point measured by first probe 26. The front runout value is a measurement from first probe 26 at a particular data point less a measurement from third probe 30 when first probe 26 is at that data point. To obtain a single value for the front runout, a minimum front runout value is subtracted from a maximum front runout value. A back runout value is determined for each data point measured by second probe 28. The back runout value is a measurement from second probe 28 at a particular data point less a measurement from fourth probe 32 when second probe 28 is at that data point. To obtain a single value for back runout, a minimum back runout value is subtracted from a maximum back runout value. A concentricity value is determined at each data point measured by first probe 26. The concentricity value for a particular data point is determined by dividing by four the result of subtracting the back runout value at that data point from the front runout value at that data point. A single concentricity value can be obtained by subtracting a minimum runout concentricity value from a maximum concentricity value.

A second measure of mechanical runout is out of roundness, which is a measure of the consistency of a circle diameter. An out of roundness value for proximity surface 16 is determined at each data point measured by first probe 26. An out of roundness value for a particular data point on proximity surface is determined by adding a measurement from first probe 26 at that data point to a measurement from second probe 28 at that data point. A single value for out of roundness for proximity surface is obtained by subtracting a minimum out of roundness value from a maximum out of roundness value. An out of roundness value for journal surface 14 is determined at each data point measured by third probe 30. The out of roundness is determined by adding a measurement from third probe 30 at that data point to a measurement from fourth probe 32 at that data point. A single value for out of roundness of journal 14 is obtained by subtracting a minimum out of roundness value from a maximum out of roundness value.

Electrical runout is a measure of error introduced by using a proximity probe 20. An electrical runout value is determined for each data point measured by first probe 26. The electrical runout value for a particular data point is a measurement from proximity probe 20 when first probe 26 is at that point less a measurement from first probe 26 at that point. In other words, the electrical runout is the difference in signals between probe 20 and probe 26. A single value for electrical runout is obtained by subtracting a minimum electrical runout value from a maximum electrical runout value.

Figure 3:
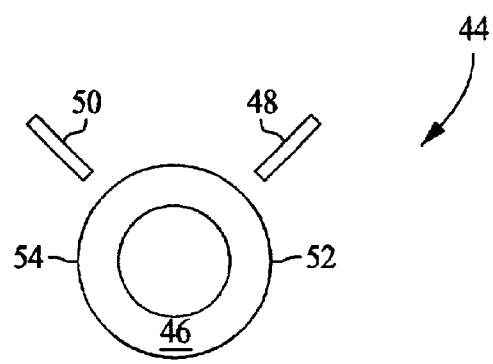
FIG. 3 is an axial view of a known slow roll assembly.

FIG. 3 is an axial view of a known slow roll assembly 44 used to test a rotating part 46 of a finished piece of rotating equipment (not shown). In an exemplary embodiment, the piece of rotating equipment is a motor and part 46 is a rotor. Slow roll assembly 44 includes a right probe 48 and a left probe 50. Alternatively, slow roll assembly can include probes at other locations, such as, for example, but not limited to, an upper and a lower probes (not shown). In other embodiments, slow roll assembly includes only one probe or more than two probes.

Figure 4:
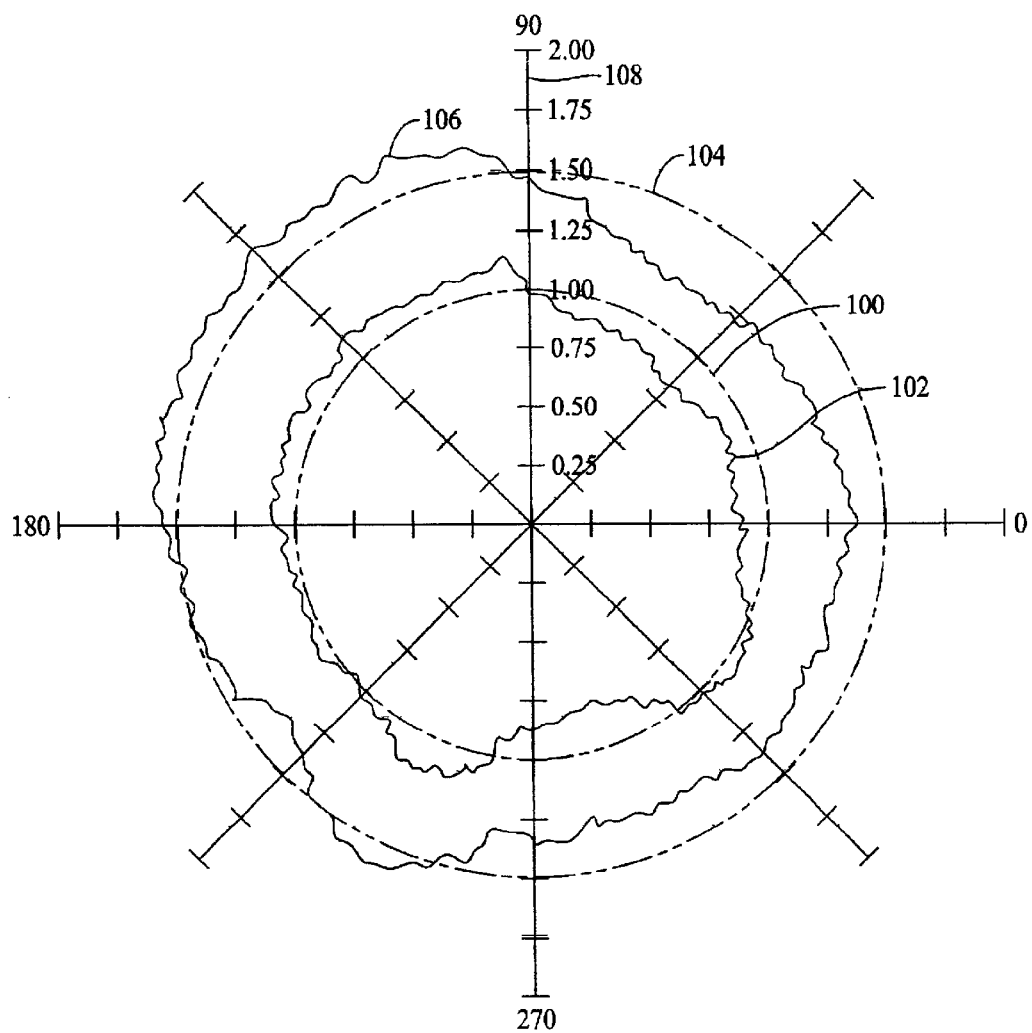
FIG. 4 illustrates data from probes presented in a format so as to provide a visual representation of the two shaft surfaces.

Following is a description of the process used to predict the readings of probes 48 and 50 in the assembled piece of rotating equipment from the data collected using probes 20, 26, 28, 30, and 32. FIG. 4 illustrates data from probes presented in a format so as to provide a visual representation of the two shaft surfaces. More specifically, FIG. 4 illustrates a theoretically perfectly round and concentric journal surface 100 and an actual shape 102 of the surface of journal 14 as measured. The shape of the journal surface 102 was determined from probes 30 and 32. FIG. 4 also illustrates a theoretically perfectly round and concentric proximity surface 104 and an actual shape 106 of the proximity surface as measured. The shape of the proximity surface 106 was determined from probes 26 and 28. FIG. 4 also includes a radial scale 108 shown in a very small scale so as to accentuate deviations from the perfect surfaces (1/1000 of an inch in this example), and an angular position (0°, 45°, 90°, 135°, 180°, 225°, 270°, and 315°).

Figure 5:
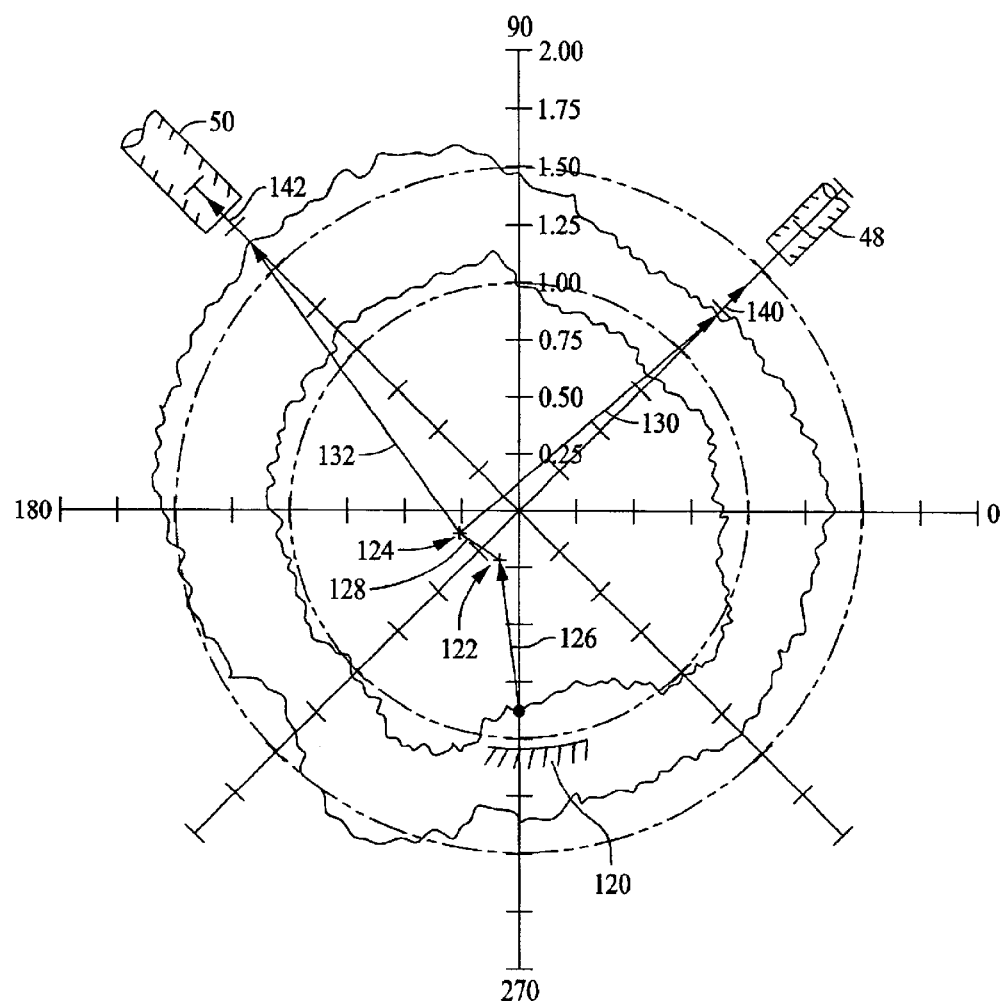
FIG. 5 illustrates how that once that the mechanical shape of the shaft surfaces is known (FIG. 4), a prediction of the proximity probe readings as experienced in the assembled machine can be made.

FIG. 5 illustrates how that once that the mechanical shape of the shaft surfaces is known (FIG. 4), a prediction of the proximity probe readings as experienced in the assembled machine can be made. FIG. 5 includes a representation 120 of the bearing surface on which the journal will contact, and a representation 122 of the geometric center of the journal surface. FIG. 5 also includes a representation 124 of the geometric center of the proximity surface, and a vector 126 from the bottom surface of the journal that is in contact with the bearing to the geometric center of the journal surface. FIG. 5 also includes a vector 128 from the geometric center of the journal to the geometric center of the proximity surface, and a vector 130 from the geometric center of the proximity surface to the proximity surface immediately under right probe 48. FIG. 5 also includes a vector 132 from the geometric center of the proximity surface to the proximity surface immediately under left probe 50, a vector 140 describing the electrical runout at the proximity surface under right probe 48, and a vector 142 describing the electrical runout at the proximity surface under left probe 50.

A prediction of the right-hand proximity probe reading of the assembled machine while the shaft is still in the lathe is made by adding vectors 126, 128, 130, and 140. A prediction of the left-hand proximity probe reading of the assembled machine is made while the shaft is still in the lathe by adding vectors 126, 128, 132, and 142. By repeating this process for each angular position for which data has been taken, the proximity probe signals can be predicted reliably, and when at least one of a single predicted slow roll runout value for left probe 50 and a single predicted slow roll runout value for right probe 48 exceeds a predetermined value, rotor 12 is re-worked until both single predicted values are less than the pre-determined value.

When rotor 12 is predicted to fail a slow roll test and at least one of a concentricity value, an out of roundness value for the proximity surface, and an out of roundness value for the journal surface exceeds at least one pre-determined tolerance then the cause is mechanical. However, when rotor 12 is predicted to fail a slow roll test and none of a concentricity value, an out of roundness value for the proximity surface, and an out of roundness value for the journal surface exceeds predetermined tolerances then the cause is electrical.

Accordingly, a method for predicting slow roll test failures is provided. At least one of an out of roundness for a journal surface, and an out of roundness for a proximity surface, and a concentricity of a rotor is measured prior to the rotor being assembled in the rotating equipment. An electrical runout is measured and a predicted slow roll runout value of the rotor is determined. The predicted slow roll value is compared to a pre-determined value and the rotor is re-worked when the predicted slow roll value exceeds the pre-determined value. Since the predicted slow roll value is determined prior to the rotating part being assembled in a piece of rotating equipment, the part is reworked prior to an initial assembly and a disassembly of the equipment is avoided, thus, saving time and expense.

Additionally, as explained above, a method for separating electrical runout from mechanical runout is provided. The method includes positioning at least one position probe against a rotating part, positioning at least one proximity probe adjacent the rotating part, and calculating an electrical runout based on measurements obtained from the position probe and the proximity probe. Additionally, through an addition of vectors, a prediction of whether a piece of rotating equipment will pass or fail a slow roll test is made.

While the invention has been described in terms of various specific embodiments, those skilled in the art will recognize that the invention can be practiced with modification within the spirit and scope of the claims.

What is claimed is:

1. A method for separating electrical runout from mechanical runout, said method comprising:

pre-determining tolerances of mechanical runout;

positioning at least one position probe such that the at least one position probe measures a position of a rotating part;

positioning at least one proximity probe adjacent the rotating part;

calculating an electrical runout based on measurements obtained from the at least one position probe and the at least one proximity probe;

calculating the mechanical runout based on the at least one position probe;

calculating a predicted slow roll test value; and comparing the predicted slow roll test value with the calculated mechanical runout, wherein a predicted slow roll test value of failure and a calculated mechanical runout value exceeding the pre-determined mechanical runout value is indicative of the predicted slow roll test value of failure being caused by the mechanical runout.

2. A method according to claim 1 wherein said positioning at least one position probe further comprises positioning at least two position probes 180° circumferentially separated from each other.

3. A method according to claim 2 wherein said positioning at least one proximity probe further comprises positioning at least two position probes 180° circumferentially separated from each other such that one position probe substantially co-linear in an axial direction to the proximity probe.

4. A method according to claim 1 wherein said positioning at least one proximity probe further comprises positioning at least one proximity probe adjacent at least one position probe.

5. A method according to claim 1 wherein said calculating an electrical runout further comprises calculating an electrical runout for a data point utilizing a difference between a measurement from the position probe and a measurement from the proximity probe.

6. A method according to claim 1 wherein said positioning at least one position probe comprises positioning at least four position probes against a rotating part.

7. A method according to claim 1 wherein said positioning at least one position probe further comprises positioning at least four position probes against a rotating part such that the probes are co-planer.

8. A method according to claim 1 wherein said calculating an electrical runout further comprises calculating an electrical runout based on measurements obtained from the position probe and the proximity probe utilizing a linear variable differential transformer data collection system.

* * * * *